US012637407B2

(12) United States Patent
Balzarek et al.

(10) Patent No.: US 12,637,407 B2
(45) Date of Patent: May 26, 2026

(54) PROCESS FOR THE PREPARATION OF MIXED POLYOL-CARBOXYLIC ACID ESTERSE

(71) Applicant: OXEA GmbH, Monheim am Rhein (DE)

(72) Inventors: Christoph Balzarek, Krefeld (DE); Eduard Rais, Mettmann (DE); Jens Kubitschke, Düsseldorf (DE); Roswitha Stein, Goch (DE); Julia Zimmerer, Cologne (DE); Alessa Hinzmann, Bielefeld (DE)

(73) Assignee: OXEA GmbH (DE)

( * ) Notice: Subject to any disclaimer, the term of this patent is extended or adjusted under 35 U.S.C. 154(b) by 488 days.

(21) Appl. No.: 18/274,414

(22) PCT Filed: Jan. 27, 2022

(86) PCT No.: PCT/EP2022/051905

§ 371 (c)(1),
(2) Date: Jul. 26, 2023

(87) PCT Pub. No.: WO2022/167318

PCT Pub. Date: Aug. 11, 2022

(65) Prior Publication Data

US 2024/0116846 A1 Apr. 11, 2024

(30) Foreign Application Priority Data

Feb. 3, 2021 (DE) ..................... 10 2021 102 508.7

(51) Int. Cl.
*C07C 67/08* (2006.01)

(52) U.S. Cl.
CPC .................................... *C07C 67/08* (2013.01)

(58) Field of Classification Search
CPC ................................ C07C 67/08; C07C 69/33
See application file for complete search history.

(56) References Cited

U.S. PATENT DOCUMENTS

| | | | | |
|---|---|---|---|---|
| 2014/0097379 | A1 | 4/2014 | Carr et al. | |
| 2015/0344400 | A1* | 12/2015 | Frey | C07C 67/08 560/200 |
| 2016/0207871 | A1* | 7/2016 | Kubitschke | C07C 67/08 |
| 2017/0183595 | A1* | 6/2017 | Ng | C07C 69/708 |
| 2018/0194712 | A1* | 7/2018 | Eubanks | C10M 105/38 |

FOREIGN PATENT DOCUMENTS

| | | | |
|---|---|---|---|
| DE | 2317276 | A1 | 10/1973 |

* cited by examiner

*Primary Examiner* — Pancham Bakshi
(74) *Attorney, Agent, or Firm* — M. Susan Spiering; Ochoa & Associates P.C.

(57) ABSTRACT

The present invention relates to a process for the preparation of mixed polyol-carboxylic acid esters having a molecular weight of greater than or equal to 200 g/mol and less than or equal to 1000 g/mol, wherein a polyol is reacted in an at least two-step reaction with different monocarboxylic acids in the form of monocarboxylic acids or of monocarboxylic acid anhydrides, wherein the different monocarboxylic acids are reacted with the polyol in the order of their reactivity in the esterification reaction, starting with the lowest reactivity, wherein the monocarboxylic acids with the lower reactivity are reacted at least partly as monocarboxylic acid anhydride and the monocarboxylic acid with the highest reactivity is reacted thereafter as monocarboxylic acid with the polyol. Furthermore, the present invention relates to the use of the process for the preparation of mixed polyol esters.

14 Claims, 2 Drawing Sheets

PROCESS FOR THE PREPARATION OF MIXED POLYOL-CARBOXYLIC ACID ESTERSE

CLAIM FOR PRIORITY

This application is a national phase application based on Application Number PCT/EP2022/051905. Application No. PCT/EP2022/051905, filed Jan. 27, 2022 was based on Application No. DE 10 2021 102 508.7, filed Feb. 3, 2021. The priorities of the foregoing applications is hereby claimed and their disclosures incorporated herein by reference.

TECHNICAL FIELD

The present invention relates to a process for the preparation of mixed polyol-carboxylic acid esters having a molecular weight of greater than or equal to 200 g/mol and less than or equal to 1000 g/mol, wherein a polyol is reacted in an at least two-step reaction with different monocarboxylic acids in the form of monocarboxylic acids or of monocarboxylic acid anhydrides, wherein the different monocarboxylic acids are reacted with the polyol in the order of their reactivity in the esterification reaction, starting with the lowest reactivity, wherein the monocarboxylic acids with the lower reactivity are reacted at least partly as monocarboxylic acid anhydride and the monocarboxylic acid with the highest reactivity is reacted thereafter as monocarboxylic acid with the polyol. Furthermore, the present invention relates to the use of the process for the preparation of mixed polyol esters.

BACKGROUND

Carboxylic acid esters of polyhydric alcohols, also called polyol esters (POEs), are used in technology on a large scale and in many different ways. For example, this class of substances can be used as plasticisers or lubricants. An important characteristic that speaks for the use of polyol esters results from the fact that the material properties of the resulting esters can be controlled both by the selection of the polyols and by the selection of the carboxylic acids. It is thus possible to provide substances for which the physical properties, such as boiling point, viscosity, cloud point, as well as the chemical properties, such as hydrolysis resistance or stability against oxidative degradation, can be specifically adjusted to the existing requirements in the application.

The ability to "tailor" the substance properties is particularly important for the operation of refrigeration systems. For example, compressors in refrigeration systems with fluorinated and chlorinated hydrocarbons (CFCs) as refrigerants are operated with various lubricants such as mineral oils, alkylbenzenes and synthetic hydrocarbons. However, these lubricants cannot be used with purely fluorinated hydrocarbons due to their poor or lack of miscibility with the refrigerants. For this reason, polyol esters or polyalkylene glycols (polyethers) are suitable for fluorinated refrigerants to ensure that the compressor functions permanently over a wide temperature range. In addition to miscibility, suitable lubricants must also have a suitable viscosity, high compatibility under the existing pressure and temperature conditions with the materials used in the refrigeration equipment. Due to their diversity, polyol esters can in principle fulfil these requirements by being specially adapted to the specific application conditions.

Flexible adaptability of lubricant properties is particularly useful for refrigeration systems, as the regulatory requirements for refrigerants are subject to change for environmental reasons. Due to the ban of CFC refrigerants (for example R11, R12, R22) with high ozone depletion and greenhouse potential, pure fluorinated hydrocarbons (for example R32, R410A) are increasingly used in this area:

R11

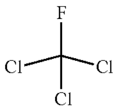

R12

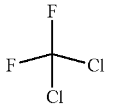

R22

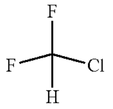

R32

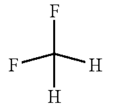

R410A

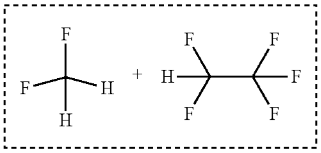

The change in the chemical composition of the refrigerants naturally also influences the physical properties and consequently an adjustment of the properties of the lubricants used together with them would be desirable.

The patent literature also contains a wide variety of processes for the production of polyol esters.

For example, DE2317276A1 discloses a process for preparing fully esterified polyols from partial esters of polyols, comprising esterifying the partial esters of polyols with an acid anhydride in the presence of a catalytic amount of a perfluoroalkylsulfonic acid or a perfluoroalkylsulfonic anhydride.

Further, DE 27 212 60 A1 discloses a two-stage process for the preparation of polyesters wherein an aromatic polycarboxylic acid selected from the group consisting of isophthalic acid and terephthalic acid is reacted with a polyol in the first stage to form a half-ester mixture, which is then reacted with a saturated or unsaturated aliphatic polycarboxylic acid in the second stage to form the polyester, wherein (a) a first portion of the polyol is contacted with the aromatic polycarboxylic acid in the first stage in at least sufficient amount to form a stirrable mixture with the aromatic polycarboxylic acid, (b) the stirrable mixture is heated to a temperature of at least 190° C., and (c) the remaining polyol portion is added to the heated stirrable mixture in such a manner that the temperature of this mixture is maintained at at least 190° C. to form a half-ester mixture.

Finally, DE 10 2012 018 207 A1 discloses a process for the preparation of polyol esters by reacting polyols with linear or branched aliphatic monocarboxylic acids having 3 to 20 carbon atoms, wherein a mixture of the starting compounds is allowed to react in the presence of a Lewis acid containing at least one element of groups 4 to 14 of the Periodic Table of the Elements as catalyst and in the presence of an adsorbent, with removal of the water formed, and the crude ester obtained is then treated by addition of a further adsorbent.

Such solutions known from the prior art can still offer further potential for improvement, especially with regard to the flexibility and controllability of the composition of the available esters.

SUMMARY OF INVENTION

It is therefore the object of the present invention to at least partially overcome the disadvantages known from the prior art. In particular, it is the task of the present invention to provide an improved process which enables the reproducible production of mixed esters in different compositions and at high conversion rates.

The problem is solved by the features of the independent claims, directed to the process and use according to the invention. Preferred embodiments of the invention are indicated in the dependent claims, in the description or in the FIGURES, whereby further features described or shown in the dependent claims or in the description or in the FIGURES may individually or in any combination constitute an object of the invention, unless the opposite clearly follows from the context.

According to the invention, the problem is solved by a process for the preparation of mixed polyol-carboxylic acid esters having a molecular weight of greater than or equal to 200 g/mol and less than or equal to 1000 g/mol, wherein a polyol is reacted in an at least two-stage reaction with different monocarboxylic acids in the form of monocarboxylic acids or of monocarboxylic acid anhydrides, wherein the different monocarboxylic acids are reacted with the polyol in the order of their reactivity in the esterification reaction, starting with the lowest reactivity, wherein the monocarboxylic acids with the lower reactivity are reacted at least partly as monocarboxylic acid anhydride and the monocarboxylic acid with the highest reactivity is subsequently reacted as monocarboxylic acid with the polyol.

Surprisingly, it was found that a large number of mixed polyol esters can be produced by means of the above-mentioned process, whereby the composition of the esters with different monocarboxylic acid contents can be determined over a wide range by means of the disclosed process control. This is particularly surprising since esterification reactions with differently reactive monocarboxylic acids generally result in only a limited number of possible compositions being available, the composition of the polyol esters obtainable without further measures being predetermined by the differences in reactivity of the individual monocarboxylic acids with the polyol. This limitation in the composition of the ester products can arise in particular when monocarboxylic acids with significantly different induction effects and/or steric requirements are to be esterified to one and the same polyol. It will always be the more reactive compared to the less reactive carboxylic acid that will add more frequently to the polyol. In the case of relatively small polyols, as indicated by the range of molecular weights, the rapid reaction of the more reactive carboxylic acid also impedes the access of the other carboxylic acids present to the remaining alcohol groups of the polyol, so that the reaction as a whole, and especially for the carboxylic acid with the lower reactivity, is significantly impeded. The reaction is also made more complex by the fact that transesterification reactions can occur in which ester compounds that have already been linked once are cleaved by exchanging the ester residues. In particular, in this case, more reactive acid residues can displace the acid residues with lower reactivity in the ester again. Complications arise in particular for cases in which all alcohol groups of a polyol should or must be reacted. In addition to the low controllability in the composition, this usually leads to inefficient, significantly prolonged reaction times and unsatisfactory controllability of the ester compositions. By the process control according to the invention, the proportions of the different monocarboxylic acids in the ester itself can be controlled and, in addition, the reaction time necessary for full conversion of the polyol can be significantly reduced by the process control according to the invention. In this respect, polyol esters with controlled, variable proportions of differently reactive monocarboxylic acids are obtainable and this under reaction conditions, here in particular reaction times, which are not known and realisable in this way under the process control methods of the prior art.

The process described is a process for the preparation of mixed polyol carboxylic acid esters having a molecular weight greater than or equal to 200 g/mol and less than or equal to 1000 g/mol. The process is concerned with the preparation of polyol esters, the polyols used being rather low molecular weight polyols. This follows from the order of magnitude of the molecular weights given above. In this respect, the process does not include the esterification of macromolecular polyols. Polyols are substances which have more than one, for example two, three or more hydroxyl groups. The individual hydroxyl groups of the molecule are converted into the corresponding esters by esterification with carboxylic acids. Preferably, the entire amount of hydroxyl groups present in the polyol can be converted into the corresponding ester groups in the process. Thus, in particular, full esters of the polyols can be obtained. The carboxylic acids used for esterification are monocarboxylic acids. At least two different monocarboxylic acids may be used. However, it is also possible that three or more monocarboxylic acids are used. In these cases, there is a "most reactive" and a "least reactive" monocarboxylic acid, the former being added to the esterification reaction as a monocarboxylic acid and the latter, at least in part, as an anhydride. In the case of a reaction of three different monocarboxylic acids, the "middle" carboxylic acid can then be added to the reaction solution either as a carboxylic acid or an anhydride or as a mixture thereof. The monocarboxylic acids may bear aliphatic or aromatic moieties and the monocarboxylic acids may, for example, have a molecular weight greater than or equal to 30 g/mol and less than or equal to 250 g/mol. The aliphatic or aromatic radicals may have functional groups or substituents other than carboxylic acid groups.

A possible reaction according to the invention may involve, for example, the esterification of a pentaerythritol molecule. This polyol can, for example, be esterified with a short-chain monocarboxylic acid (iso-C4) and a long-chain monocarboxylic acid (iso-C9). In principle, five different tetra-esters can be formed depending on the stoichiometry and reactivity of the individual carboxylic acids (equation not stoichiometric):

Reaction equation 1

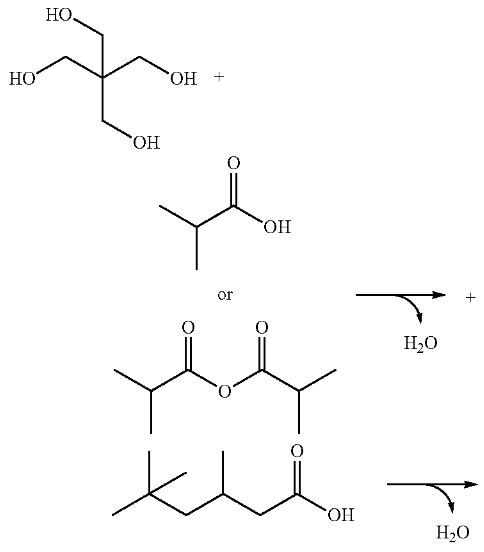

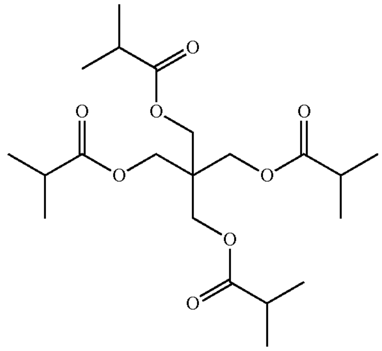

PE4444

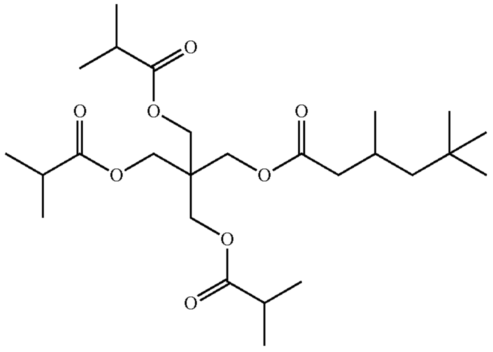

PE4449

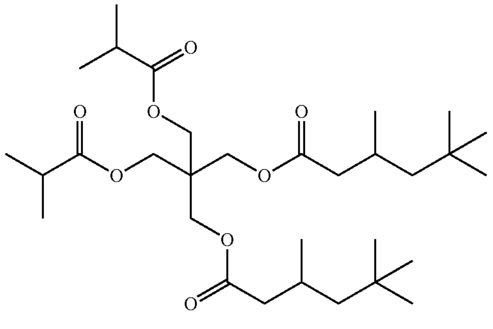

PE4499

-continued

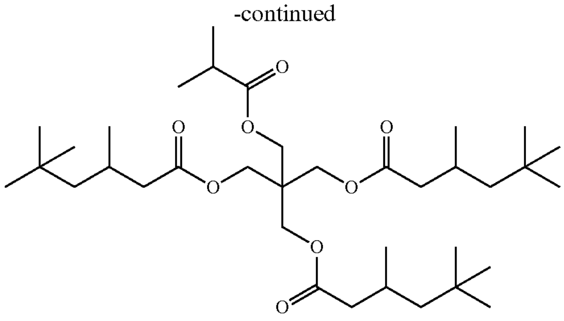

PE4999

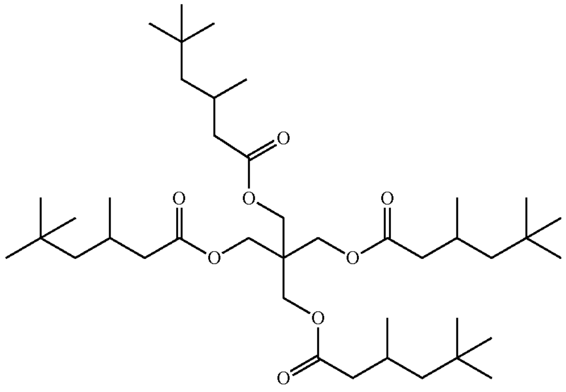

PE9999

The five different tetra-esters are examples of polyol esters formed in the course of the reaction according to the invention. The composition and specific number of the esterified carboxylic acids is determined in principle by the reactivity of the individual monocarboxylic acids and additionally, according to the invention, by the process control. The proportions of the esterified different carboxylic acids are related to the sum of the mixed polyol esters formed in the process according to the invention.

In the process described, a polyol is reacted with various monocarboxylic acids in the form of monocarboxylic acids or of monocarboxylic acid anhydrides in an at least two-stage reaction. Thus, the esterification of the polyol is not carried out within a simple reaction in which the hydroxyl groups are reacted with only one carboxylic acid or carboxylic acid mixture. The reaction comprises at least the use of two different monocarboxylic acids, each of the individual monocarboxylic acids being used either in the form of a carboxylic acid or in the form of a monocarboxylic acid anhydride:

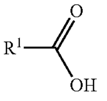

Carboxylic acid

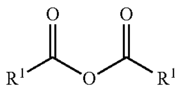

Anhydride

The carboxylic acid anhydride results from the reaction of two identical monocarboxylic acids under removal of water. The reaction takes place in two stages in that at least once during the reaction the composition of the reaction environment is actively changed by an external intervention. Thus, in the course of the reaction, one or more substances are added to the already progressing reaction. The "normal" progress of the reaction by conversion of the reactants to the products does not count as an active change of the reaction environment. In addition, there is a period of time in which the reaction solution only comprises one of the monocarboxylic acids/anhydrides. Possible monocarboxylic acids can be selected, for example, from the group consisting of straight-chain or branched C3-C25 monocarboxylic acids.

The different monocarboxylic acids are reacted with the polyol in the order of their reactivity in the esterification reaction, starting with the lowest reactivity. The contacting and reaction of the polyol with the different monocarboxylic acids is not carried out randomly, but as a function of the reactivity of the individual monocarboxylic acids with the polyol. The reactivity in this context refers to the reaction rate of the esterification of the monocarboxylic acid in question with the polyol. For this purpose, the reaction rate of a simple reaction of the monocarboxylic acid with the polyol can be determined, for example. The methods for determining the reaction rate of an esterification reaction are known to the skilled person. For example, the reaction rate can be determined using spectroscopic methods that can quantitatively monitor the occurrence of ester groups. The esterification reaction is carried out independently with the one and the other carboxylic acid. The reaction conditions, such as the temperature and the molar quantities used, are to be kept constant for the two different determinations of the reaction rate. Regardless of the esterification reaction conditions chosen, a ratio between the two reactivities of the monocarboxylic acids can always be determined in relation to the esterification reaction present. From the rate comparison, a relation is obtained that one of the monocarboxylic acids is more reactive and the other monocarboxylic acid is less reactive. Should different reactivities occur as a function of the reaction conditions, for example under extreme temperature or pressure conditions, the reaction rates measured with the same composition in a temperature interval of 20° C. to 30° C. and under normal pressure are decisive for determining the reactivities. The monocarboxylic acid with the lower reactivity is contacted in the esterification reaction with the polyol present before the monocarboxylic acid(s) with higher reactivities in terms of time. This can be achieved, for example, by adding the monocarboxylic acids with higher reactivities later to the reaction solution with the polyol. In this respect, according to the invention, an esterification reaction of the polyol with part or all of the monocarboxylic acid with the lowest reactivity is always carried out first in the esterification reaction in question, whereby the esterification reaction does not have to lead to complete reaction of the monocarboxylic acid with the lowest reactivity before addition of the further carboxylic acids. It is sufficient that the carboxylic acid or the further carboxylic acids are already added to the reaction solution before a complete reaction of the carboxylic acid with the lowest reactivity.

The monocarboxylic acids with the lower reactivity are at least partially reacted with the polyol as monocarboxylic acid anhydride and the monocarboxylic acid with the highest reactivity is subsequently reacted with the polyol as monocarboxylic acid. To control the composition of the polyol ester, at least some of the monocarboxylic acids with the lower reaction rate in the esterification reaction are added to the reaction solution as monocarboxylic acid anhydride. The anhydride portion of the monocarboxylic acids with the lowest reactivity can thereby preferably be greater than or equal to 25 mol %, preferably greater than or equal to 50 mol % and further preferably greater than or equal to 90 mol %. Preferably, this monocarboxylic acid can also be added in the form of 100 mol % as an anhydride. This addition in the form of an anhydride is at first unusual, since at this point we are dealing with a "simple" system consisting only of the polyol and the monocarboxylic acid with the lowest reactivity. However, it has been shown that the stoichiometry of the esterification can be controlled to a large extent by using it as an anhydride. In this respect, not only faster but also different compositions of esters of the polyol are obtained. In the process proposed here, the most reactive monocarboxylic acid is then added at a later stage and not as an anhydride. This process control has proved to be favourable, although it could have been assumed that the addition of the most reactive monocarboxylic acid should also be in the form of anhydrides. However, this has proved to be disadvantageous in the context of the present process. If mixed esters of more than three different monocarboxylic acids are to be produced in the process, the carboxylic acid with the "medium" reactivity can be added either in the form of the carboxylic acids themselves or as an anhydride. It is essential that the least reactive monocarboxylic acid is added, at least in part, as an anhydride and the most reactive monocarboxylic acid is added in acid form.

DETAILED DESCRIPTION

Figure 1:
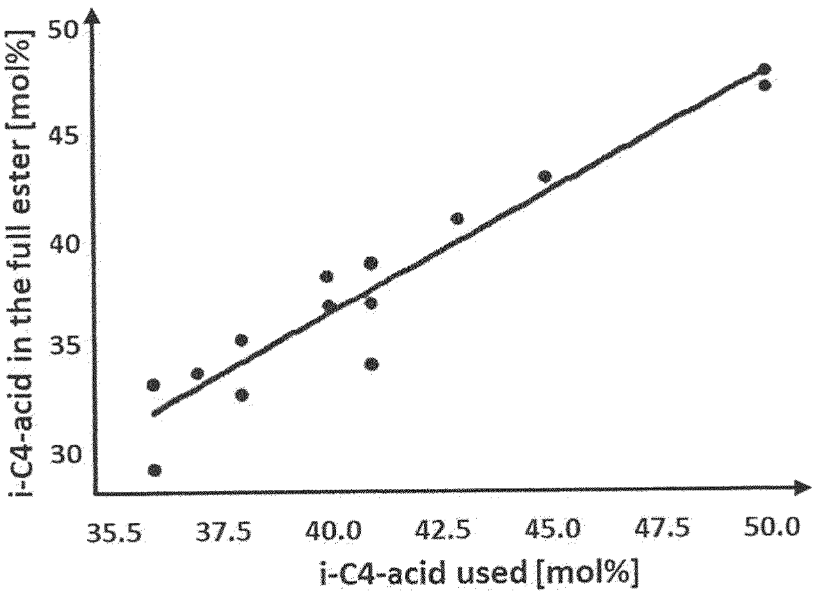
FIGS. 1 and 2 show the changes in the composition of obtainable esters with simultaneous use of an i-C4/i-C9 carboxylic acid mixture as a function of the acid educt amounts (conditions: 20 mol % excess acid, max. 250° C., 30 h esterification).

In a preferred embodiment of the process, two different monocarboxylic acids can be reacted with the polyol, whereby in the first step, the monocarboxylic acid with the lower reactivity is reacted with the polyol in an amount greater than or equal to 70 mol % as a monocarboxylic acid anhydride. The process presented here has proven to be particularly suitable for the preparation of mixed polyol esters from two different monocarboxylic acids. In this respect, mixed polyol esters are obtained which carry two different ester groups. In order to obtain the fastest possible reaction and to control the ester content of the carboxylic acid with the lower reactivity, the above-mentioned minimum content of anhydride has proven to be particularly suitable.

In a further preferred embodiment of the process, the less reactive monocarboxylic acid can be reacted with the polyol as a monocarboxylic acid anhydride in the first step and the more reactive monocarboxylic acid as a monocarboxylic acid in a second step. For the fastest possible overall conversion and for the precise control of the individual proportions of the different carboxylic acids, it has proved particularly favourable that the less reactive monocarboxylic acid is only added to the reaction as an anhydride. This measure, together with the use of the more reactive monocarboxylic acids only as monocarboxylic acid without anhydride portion, can in combination also lead in particular to ester compositions being obtained which are neither obtainable by the use of monocarboxylic acids alone nor by the use of anhydrides in the second reaction step for the more reactive carboxylic acid.

Within a preferred characteristic of the process, the polyol may have greater than or equal to 2 and less than or equal to 8 OH groups. The process presented herein may be particularly suitable for polyols with a small to medium number of hydroxyl groups. The composition of the different carboxylic acids on these rather small polyols is particularly challenging due to the spatial constraints in the conversions. In particular, in these cases where there are relatively few hydroxyl groups on the molecule, and these hydroxyl groups are also not far apart, there can be particular difficulties in the conversion of monocarboxylic acids, especially in cases where they have different reactivities. These differences may arise on the basis of the structures of the monocarboxylic acids, for example alpha-branched or non-alpha-branched carboxylic acids, or due to induction effects, for example the size of the +i effect of the alkyl chain. Without being bound by theory, this may in particular be due to the fact that the access of further monocarboxylic acids to the hydroxyl groups of the polyol is significantly impeded by the esterified groups already present. In these constellations, the proposed process can lead to compositions being obtainable which, without the proposed process control, could not be obtained at all or only under very harsh reaction conditions susceptible to by-product formation. Preferably, the polyol having the OH group number indicated above may have a molecular weight greater than or equal to 80 g/mol and less than or equal to 700 g/mol, further preferably greater than or equal to 90 g/mol and less than or equal to 600 g/mol. The polyols in the indicated molecular weight ranges may preferably carry three, four, five or even six OH groups.

According to a preferred embodiment of the process, the polyol can be an aliphatic polyol with a molecular weight of greater than or equal to 50 g/mol and less than or equal to 400 g/mol. For aliphatic polyols which accordingly have no aromatic groups, particularly flexible esters with widely varying ester compositions can be obtained via the process according to the invention. This is difficult for aliphatic polyols in the molecular weight range indicated above according to the prior art processes, since these polyols are relatively small polyols in which esterification with several monocarboxylic acids leads to significantly altered spatial stresses around the polyol. In particular, full esterification is difficult for this class of polyol because as the additional hydroxyl groups are esterified, the space available around the polyol decreases significantly, making it much more difficult for additional carboxylic acids to enter the ester reaction. Preferably, the polyol may have a molecular weight of greater than or equal to 100 g/mol and less than or equal to 300 g/mol and further preferably a molecular weight of greater than or equal to 120 g/mol and less than or equal to 250 g/mol. For these polyols, the process presented can lead to particularly accelerated reactions and in particular to esters with higher proportions of the less reactive carboxylic acid.

In a preferred aspect of the process, the different reaction steps can be carried out without work-up in only one reaction solution. For fast and efficient reaction control, it has been found to be particularly suitable that the process is carried out as a "one-pot" reaction in only one reaction solution. By means of the indicated process control, the desired compositions of ester groups on the polyol can be determined with only a slight deviation. Furthermore, time and cost-intensive work-up of the reaction solution can be avoided in this way. In this case, in only one reaction solution means that certain reactants can also be added to this one reaction solution at a later time. Not all reactants have to be present in the reaction solution at the same time at the beginning of the reaction.

According to a further preferred embodiment of the process, the esterification can be carried out without the addition of an esterification catalyst. Surprisingly, it was found that the process according to the invention, with a delayed addition of the second carboxylic acid in carboxylic acid form and the use of the less reactive carboxylic acid as an anhydride, completely eliminates the need for an esterification catalyst. The possible acceleration of the reaction by an esterification catalyst is not significantly faster compared to a process without a catalyst and thus the disadvantages that the catalyst has to be separated from the desired product at the end of the reaction outweighs.

In a preferred aspect of the process, the less reactive monocarboxylic acid can be present in the form of an anhydride and first reacted with only part of the polyol, with the remaining part of the polyol subsequently being added together with the monocarboxylic acid(s) with the higher reactivity. For fast and reproducible process control, it has proven to be particularly suitable that at the beginning of the reaction only a part of the polyol is introduced and reacted with the more reactive reactant in the form of an anhydride. Only in the second stage, after a certain reaction time, the rest of the polyol is then added to the partial solution of the first stage together with the less reactive monocarboxylic acid as anhydride and the more reactive carboxylic acid in acid form. Without being bound by theory, this apparently allows a more uniform esterification to take place, highly probably by keeping the viscosity of the reaction solution particularly low, especially at the beginning. By influencing the rheology of the solution, an improved mixing of the solution can result.

According to a preferred embodiment of the process, the less reactive monocarboxylic acid can be a branched monocarboxylic acid with an alkyl radical in the alpha position to the carboxylic acid group and the more reactive monocarboxylic acid can be a branched or unbranched C4-C18 monocarboxylic acid without an alkyl radical in the alpha position to the carboxylic acid group. In particular, the esterification of a relatively small polyol with monocarboxylic acids having above-mentioned differences in their structure can be particularly challenging according to prior art methods. Substitution in the alpha position can result in the monocarboxylic acid forming an ester bond with polyols only extremely poorly and slowly. This can also be the case if the monocarboxylic acid otherwise has only a very small aliphatic backbone. The blocking of the alpha position results in a clear difference in reactivity even to larger aliphatic monocarboxylic acids with up to twelve carbon atoms. Irrespective of the reaction control, according to the prior art the proportions of the individual carboxylic acids can only be realised very slowly with these preconditions and without a control of the individual proportions of the different carboxylic acids. By the process according to the invention, in particular, the proportions of the carboxylic acid with blocking in the alpha position can also be significantly increased. In addition, for a given target composition, the reactions take place significantly faster via the process according to the invention compared to the use of only monocarboxylic acids and without an anhydride component.

Within a further preferred aspect of the process, the less reactive monocarboxylic acid may be iso-butyric acid and the more reactive monocarboxylic acid may be iso-nonanoic acid. In particular, the esterification of iso-butyric acid and iso-nonanoic acid can only be used to produce an extremely limited number of different polyol esters under the reaction conditions of the prior art. The difference in the reaction rates of iso-butyric acid and iso-nonanoic acid on polyols, and especially on relatively "small" polyols with a molecular weight in the order of 200-300 g/mol, leads to only unsatisfactory results, since for the most part the iso-nonanoic acid and not the iso-butyric acid is added to the polyol. Different process control with different temperatures and different proportions of the individual carboxylic acids cannot significantly improve this result. The conversions take a very long time, especially in cases where a full conversion of the polyol is needed. In addition, the iso-butyric acid fraction, and thus indirectly the iso-nonanoic acid fraction, cannot be varied. This is not the case with the process according to the invention. Significantly higher reaction rates result and, in particular, the iso-butyric acid ester content in the polyol can also be significantly increased.

Within a preferred embodiment of the process, the molar ratio of polyol to the less reactive monocarboxylic acid and the molar ratio of polyol to monocarboxylic acid of the most reactive monocarboxylic acid, expressed in each case as mol of the respective component/mol of polyol, can be greater than or equal to 1 and less than or equal to 3.5. For reproducible control of the reaction and to obtain the lowest overall possible reaction times, it has proven to be particularly favourable that the different carboxylic acids are used in total in an approximately equal molar concentration range with respect to the polyol in the reaction solution. In these cases, the different composition can be controlled particularly favourably by the time of addition and the temperature control during the reaction. The ratio applies after addition of the entire amount of the different carboxylic acids to the reaction solution. It is surprising that with an approximately equal amount of the different carboxylic acids a wide range of different polyol esters can be realised. This was not to be expected, since despite different reaction rates, the concentration of the individual monocarboxylic acids is directly proportional to the reaction rate of ester formation. In the case of use of the monocarboxylic acid as an anhydride according to the invention, one mole of anhydride corresponds to two moles of the monocarboxylic acid.

In a preferred aspect of the process, the temperatures in the different reaction steps may be different, with the temperature in the first esterification step of the monocarboxylic acids with the lower reactivity in the form of anhydrides being greater than or equal to 50° C. and less than or equal to 100° C. below the temperature in the final esterification step of the monocarboxylic acids. In order to obtain the most efficient process control, it has been found to be particularly suitable that the temperature in the first process step, i.e., when adding the less reactive monocarboxylic acid in the form of an anhydride, is lower than the temperature in the second process step. Despite the reduction in temperature, significant reaction rates result for the overall reaction, so that this process control leads, for example, to faster overall conversions of the polyol compared to the processes described in the prior art. The temperature range specified above is also suitable for significantly reducing the proportion of "undesirable" esters, such as polyol esters with other, undesirable ester compositions. This results in a well-controllable and highly efficient esterification reaction.

Furthermore, according to the invention is to use of the process according to the invention for the preparation of mixed polyol esters comprising at least two different ester groups and a hydroxyl number greater than or equal to 0 and less than or equal to 10. The process according to the invention may be particularly suitable for obtaining polyol esters which carry only a very small proportion of still free hydroxyl groups. Accordingly, the mixed polyol esters carry ester groups of different monocarboxylic acids, one of the monocarboxylic acids being a less reactive component and the other monocarboxylic acid being a more reactive component. The preparation of mixed polyesters with two different ester groups can be challenging in the prior art, as the esterification becomes slower during the course of the reaction of the polyols due to the higher spatial stress and the possibilities of transesterification reactions increase. Production of polyol esters within reasonable reaction times is not achievable for this prior art embodiment. This is particularly true for relatively small polyols with a molecular weight greater than or equal to 80 g/mol and a molecular weight less than or equal to 400 g/mol. These relatively small polyols may carry, for example, from three to five hydroxyl groups. For this group of polyols in particular, quantitative esterification with correspondingly small hydroxyl numbers is extremely difficult to achieve. The hydroxyl number of the esters can be determined by a method known to the skilled person, for example according to DIN 53240-2.

In a preferred embodiment of use, the mixed polyol ester can be an iso-butyric acid/iso-nonanoic acid ester of pentaerythritol. Particularly in the case of the pentaerythritol ester or the pentaerythritol tetra-ester, an esterification reaction with iso-butyric acid and iso-nonanoic acid can only be carried out within a narrowly limited range and under long reaction times according to the prior art. It is not possible to predetermine the amounts of the different ester groups on the polyol and mainly esters with a clear iso-nonanoic acid excess result. This may be undesirable for certain applications, as the physical properties of the ester, such as viscosity, cannot be adapted to the required needs. By carrying out the process according to the invention, the iso-butyric acid content in the polyol ester in particular can be increased and thus the physical and chemical properties of the obtainable esters, and of course also of the full esters, can be controlled over a wide range and obtained within short reaction times.

In a further preferred characteristic of the use, the polyol ester may have greater than or equal to 20 mol % and less than or equal to 50 mol % iso-butyric acid groups and greater than or equal to 50 mol % and less than or equal to 80 mol % iso-nonanoic acid ester groups. Due to the differences in reactivity of the above carboxylic acids, it is usually the case that the mixed polyol esters have higher iso-nonanoic acid ester groups contents. Via the process and use according to the invention, the proportion of iso-butyric acid ester groups in the mixed polyol ester can be significantly increased. Moreover, the increase in the proportion of iso-butyric acid ester groups can be obtained within very short reaction times. The further advantage is that the amount of iso-butyric acid ester groups within the ranges given above can be controlled particularly precisely, especially for full esters. The addition of the anhydride of the more reactive monocarboxylic acid in the first step results in a different distribution of the obtainable mixed polyol esters compared to the use of the less reactive monocarboxylic acid in the acid form. By using the anhydride, mixed polyol esters are formed with the desired higher proportion of the less reactive esterified monocarboxylic acid. In this respect, mixed polyol esters with different chemical and physical properties can be obtained, whereby significantly shorter reaction times are obtainable via the use of the lower reactivity carboxylic acid in the form of an anhydride according to the invention. In particular, the polyol full ester can be a pentaerythritol tetra-ester.

Further details, features and advantages of the subject-matter of the invention are apparent from the dependent claims and from the following description of the figures and associated examples.

EXAMPLES

An esterification is usually carried out at higher temperatures under reflux and with a water separator in order to remove the reaction water produced in the reaction, at least partially, from the reaction solution.

The examples according to the invention are shown on the basis of a reaction of iso-butyric acid (i-C4) with a branching in the alpha position to the carboxyl group as a less reactive acid and iso-nonanoic acid (i-C9) without branching in the alpha position to the carboxyl group as a more reactive carboxylic acid. The esterification of i-C4 in particular poses a challenge in ester production according to the prior art, as it has a high solubility in water (about 210-265 g/L at 20° C.) and a relatively low boiling point (154° C., 1013 mbar). The i-C4 is completely miscible with water above 26° C. and forms an azeotrope with water (approx. 72-79% water) with a boiling point of approx. 99° C. Accordingly, the reflux of the reaction mixture starts early and i-C4 returns together with water from the water separator to the reaction site, so that the equilibrium is partially shifted towards the reactant side again. Structurally, the i-C4 has a methyl group in the alpha position, which sterically hinders the esterification, so that significantly more time is needed for a complete polyol conversion or this is even completely prevented.

The polyol component used in the examples is pentaerythritol (PE), a low molecular weight aliphatic polyol with 4 OH groups.

I. Esterification According to the State of the Art

Figure 2:
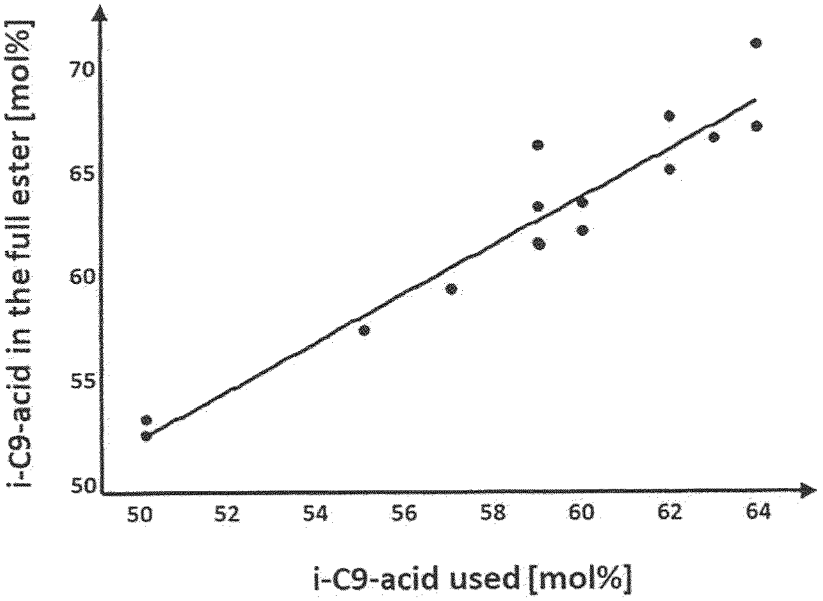

I.a One-Pot Esterification with Simultaneous Use of Both Carboxylic Acids According to the State of the Art FIGS. 1 and 2 show the changes in the composition of obtainable esters with simultaneous use of an i-C4/i-C9 carboxylic acid mixture as a function of the acid educt amounts (conditions: 20 mol % excess acid, max. 250° C., 30 h esterification). In the investigated area, i-C4 was found in the tetra-ester to a lesser extent (approx. 3.4 mol % less) than would be expected from the reactant input in the acid mixture. Possible reasons for this are the loss of the carboxylic acid with the reaction water and the overall lower reactivity of i-C4 compared to i-C9. In addition, the reaction times for the complete conversion of all OH groups of the polyols are quite long at 30 h.

The loss of the i-C4 with the reaction water poses a problem in these conversions, as the organic components have to be removed from the wastewater stream at great expense. In addition, as already mentioned above, the removal of a reactant from the equilibrium is detrimental to the reaction rate and the composition of the final product.

I.b One-Pot Esterification with Simultaneous Use of Both Carboxylic Acids and an Organic Entrainer According to the State of the Art The esterifications were carried out in a multi-neck round-bottom flask connected to a Dean-Stark apparatus for water separation. The mass of the aqueous phase after the reaction was 12 wt % higher than the theoretical value. A water content of 86 wt % was found, which corresponds to only 96% of the reaction water in the aqueous phase. The remaining water is either lost via the gas flow or is still present dissolved in the organic phase. The remaining 14 wt % of the aqueous phase is predominantly iso-butyric acid and a small amount of iso-nonanoic acid.

To avoid high reactant contents in the reaction water and to accelerate the reaction, the use of water entraining agents could be conceivable. The above experiment was repeated with different water entraining agents (durol, naphthalene and tetrahydronaphthaline). Despite the use of the entraining agents, the water content of 85% by weight in the aqueous phase could not be further increased. Thus, the use of water entrainer is not an alternative to accelerate and simplify the reaction.

I.c One-Pot Esterification with Transesterification of a Full Ester According to the State of the Art Transesterifications were also tested to avoid the accumulation of water and the associated acid losses. A reaction of methyl isobutyrate with pentaerythritol could not be observed after 4 h at92° C.:

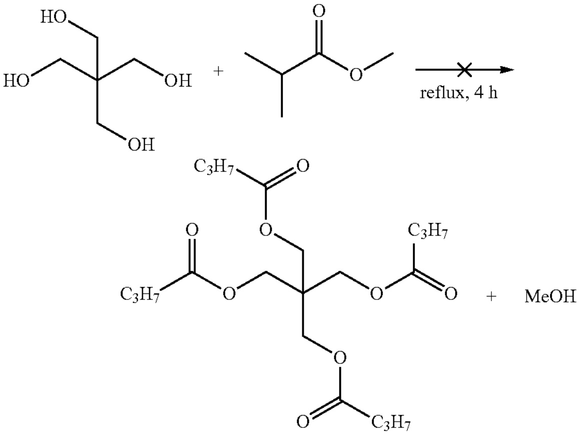

Transesterification experiments with pentaerythritol-based iso-C9 ester and i-C4 at a temperature of approx. 130° C. and 6 h reaction time show that the composition of the polyol ester changes only slightly.

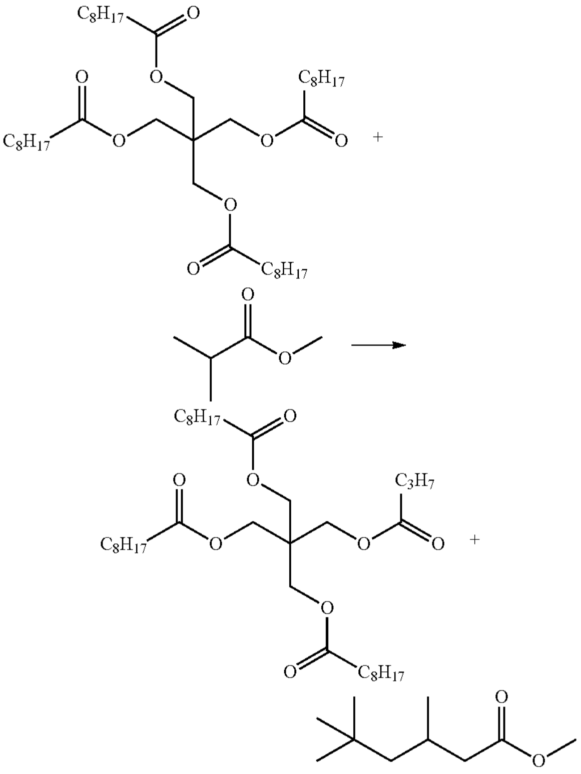

Transesterification experiments with pentaerythritol-based iso-C9 ester and i-C4 show that an acid exchange takes place. However, transesterification with i-C4 shows only a slight change in composition at 168° C. and 20 h reaction time, although the amount of i-C4 added is 50 mol % with respect to the OH groups of the polyol. Also the use of different Lewis acid catalysts or sodium acetate shows no significant difference to the reference reaction without catalyst.

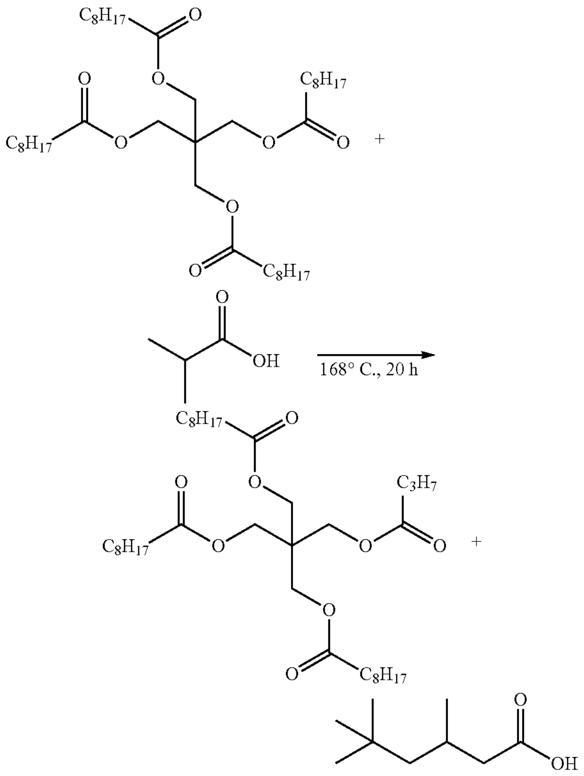

A significant change in the composition of the esters using a transesterification is not possible within reasonable reaction times and reaction conditions.

I.d Sequential Esterification According to the State of the Art

Based on the relatively long reaction times for the simultaneous esterification of i-C4 and i-C9 with pentaerythritol and due to the low tendency to transesterification, experiments on sequential esterification are carried out. In these, the less reactive i-C4 is first reacted with the pentaerythritol and only then, in a second step, the remaining hydroxyl groups of the polyol are esterified with the more reactive i-C9 using higher temperatures:

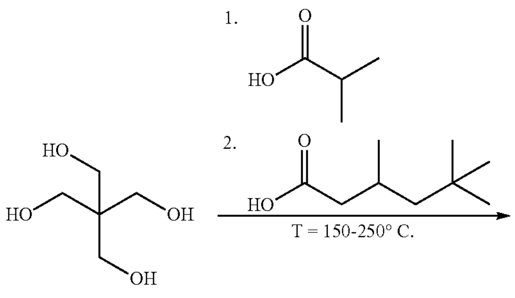

-continued

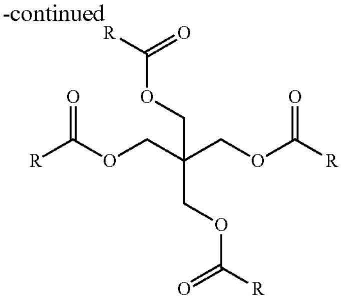

R = $C_3H_7$ or $C_8H_{17}$

By means of the experiment, an ester composition with more than 30 mol-% i-C4 on the polyol is to be adjusted.

In the experiment, the polyol (pentaerythritol) is reacted with the i-C4 acid in the first 5 h. To avoid acid losses in the reaction water (Dean-Stark apparatus), a reaction temperature below the boiling point of the i-C4 is selected. After 5 h, i-C9 acid is added and heated up to 250° C. for another 20 h. The amount of water formed within 5 h is then reduced. The amount of water formed within the first 5 h is only 29% of the theoretical amount, which indicates a very slow conversion of i-C4. After the addition of i-C9, an additional 69% of the theoretical amount of water is formed. The missing 2% of the theoretical amount of water was found in the organic phase in the Dean-Stark apparatus. The analysis of the ester after the mainstrip showed an OH number of 0.5 mg KOH/g, with a content of 33 mol % iso-butyrate and 67 mol % iso-nonanoate.

By means of relatively long reaction times, a mixed full ester can be obtained, whereby the desired quantity ratio is not obtained within the given reaction times and under the temperatures by using the corresponding amounts of reactants. The less reactive component i-C4 is only esterified sub-stoichiometrically with the OH groups of the polyol.

I.e Simultaneous 1-Step Esterification Using an Anhydride of the Less Reactive Component A one-pot experiment is carried out using iso-butyric anhydride and i-C9. After 30 min and at a reaction temperature of 150° C., a GC analysis shows that a mixture of different anhydrides is formed in the reaction solution:

| | [%] |
|---|---|
| low-boiling components | 7.68 |
| iso-$C_4$ acid | 11.89 |
| iso-$C_4$-acid anhydride | 2.06 |
| iso-$C_{13}$ anhydride (?) | 9.88 |
| iso-$C_9$ acid | 50.23 |
| iso-$C_9$-acid anhydride | 18.07 |
| high-boiling components | 0.19 |

A simultaneous use of iso-butyric anhydride and iso-nonanoic acid is therefore disadvantageous, as the higher reactivity of iso-nonanoic acid causes the formation of mixed anhydrides.

II. 2-Step Esterification According to the Invention Using an Acid Anhydride in the First Step In preliminary tests with iso-butyric anhydride and pentaerythritol, it was found that there is a high reactivity and therefore the reaction temperature may only be increased carefully. The boiling point of iso-butyric anhydride is 183° C., the boiling point of the iso-butyric acid released during esterification is 156° C. A reaction of the carboxylic acid anhydride with the pentaerythritol could suddenly produce large amounts of iso-butyric acid. If the reaction temperature is already above 156° C. at this point, boiling distortions may occur. Due to the rapid reaction, a temperature below 156° C. can also rise above the boiling point of the short-chain acid within a short time due to the release of energy.

According to the invention, esterifications are carried out in which the pentaerythritol is first reacted with iso-butyric acid anhydride. The amount of acid anhydride and pentaerythritol is used in a molar ratio, as in a hypothetical ester synthesis aiming at an iso-C4 content of more than 30 mol % in the ester, i.e., with an excess of acid. The reaction is carried out at 150° C. for 4 h. Then iso-nonanoic acid is added and the esterification is carried out for another 16 h at max. 250° C. The esters obtained have a hydroxyl value of 3.5 and 3.8 mg KOH/g, respectively, and consequently almost complete esterification of the polyol is achieved. Furthermore, it can be shown by IR spectrometry that the spectra recorded during the reaction show hardly any differences after more than 30 min after the start of the experiment in the first stage at a temperature of up to 150° C. This indicates that the esterification of the polyol is almost complete. This is an indication that at this time there is already a high reaction progress in the esterification of the i-C4 component as anhydride. After 4 h, no more iso-butyric anhydride could be found in the mixture by gas chromatography.

A comparison of a 2-step process according to the invention with anhydride in the first step compared to a process not according to the invention without anhydride shows that the anhydride offers a speed advantage over the acid in the sequential conversion of the pentaerythritol. In addition to the different OH numbers, the esters also differ in the iso-C4 content. Due to the higher reactivity of the anhydride, a product is obtained after esterification that has a higher iso-C4 content in the ester (~5 mol %) compared to the use of a pure acid mixture.

| 30 min at 150° C. + 20 h at max. 250° C. | Acid only | according to the invention |
|---|---|---|
| Pentaerythritol [g] | 100 | 100 |
| Pentaerythritol [mol] | 0.735 | 0.735 |
| iso-$C_4$ acid [g] | 115 | — |
| iso-$C_4$ acid [mol] | 1.305 | — |
| iso-$C_4$ anhydride [g] | — | 103.2 |
| iso-$C_4$ anhydride [mol] | — | 0.652 |
| iso-$C_9$ acid [g] | 351.4 | 351.4 |
| iso-$C_9$ acid [mol] | 2.221 | 2.221 |
| iso-$C_4$ content (ester) [mol %] | 29 | 34 |
| Esterification time [h] | 20.5 | 20.5 |
| Reaction temperature [° C.] | 150-250 | 150-250 |
| OH number [mg KOH/g] | 11 | 4 |

From the table it can be seen that within the same reaction time and within the same reaction temperature range not only a more complete conversion, recognisable by the lower OH number, but also a significantly higher iso-C4 content in the ester is obtained. Surprisingly, these advantages are maintained even though the temperatures and reaction times of the i-C9 esters are greater and thus strong transesterification reactions should proceed preferentially, which should significantly reduce or completely render obsolete an influence of the first reaction step.

III. 2-Step Esterification According to the Invention Using an Acid Anhydride in the First Step—Kinetic Considerations The process according to the invention is intended to produce mixed i-C4/i-C9 esters with a high i-C4 content. The first reaction step was carried out using i-C4 anhydride at a reaction temperature of 170° C. In each case 5 experiments were carried out. The mean values of the C4 proportions and the standard deviations over the series of experiments are given:

| i-C4 anhydride Reaction time in h | i-C9 acid Reaction time in h | Proportion C4 ester [mol %] (Stabw.) | OH number |
|---|---|---|---|
| 1 | 2 | 43 (4.2) | 34 |
| | 3 | 40 (0.9) | 20.7 (6.0) |
| | 4 | 39 (1.4) | 10.4 (3.1) |
| | 5 | 38 (3.1) | 8.7 (2.8) |
| | 6 | 36 (2.6) | 7.0 (1.5) |
| | 7 | 36 (1.9) | 7.9 (2.7) |
| | 8 | 35 (3.7) | 5.1 (1.8) |

From the i-C4 proportions, it can be concluded that particularly high i-C4 proportions can be realised in the ester by using anhydrides in the first stage. It also becomes clear that with longer reaction times in the second stage, the i-C4 content in the resulting ester decreases again due to the competitive reaction with the i-C9 acid. Nevertheless, the esterification via anhydrides seems to be suitable for providing mixed esters with relatively high i-C4 contents in short reaction times and under moderate reaction conditions. These proportions are still in the range of more than 30 mol % i-C4 content even after 8 h reaction time with the i-C9 acid, i.e., after a total reaction time of 9 h. This proportion is clearly above those of esters processed not according to the present invention. This proportion is significantly higher than that of processes not according to the invention and also allows a significantly longer reaction time of the i-C9 acid to obtain a more complete conversion without these long reaction times giving rise to strong transesterification reactions.

To determine the kinetic effects of esterification, a comparison of a process according to the invention using i-C4 anhydride with a process not according to the invention using i-C4 acid in the esterification with PE was carried out. After one hour of reaction of the i-C4 components in the first stage, i-C9 acid was added and esterified for 3 hours in the second stage in both cases. The percentages of the mixed PE esters (for the designation see reaction equation 1) and the percentages of i-C4 in the total mixture of polyol esters are given.

| Ester composition | | Not according to the invention: 1 h i-C4 acid | According to the invention: 1 h i-C4 anhydride |
|---|---|---|---|
| Proportion [mol %] | PE444-OH | 0.11 | 0.96 |
| | PE4444 | 0.63 | 2.20 |
| | PE449OH | 0.93 | 4.71 |
| | PE4449 | 4.03 | 8.74 |
| | PE499OH | 7.50 | 9.04 |
| | PE4499 | 8.21 | 17.73 |
| | PE999OH | 21.21 | 6.78 |
| | PE4999 | 5.59 | 21.63 |
| | PE9999 | 27.67 | 11.92 |

-continued

| Ester composition | Not according to the invention: 1 h i-C4 acid | According to the invention: 1 h i-C4 anhydride |
|---|---|---|
| i-C4 content in ester components [mol %] | 26 (from 75.88) | 42 (from 83.71) |

The comparison shows that when i-C4 anhydride is used in the first stage, mixed polyol esters with a higher proportion of i-C4 are formed compared to the use of i-C4 acid. The degree of esterification when i-C4 anhydride is used in the first stage is higher after the 4 hours of the reaction compared to the use of i-C4 acid, and the reaction is more complete. It is interesting to observe that the use of i-C4 anhydride in the first stage, despite long reaction times in the second stage, leads to higher proportions of the esters such as PE4444 and PE4449. This has a positive effect on the above-mentioned i-C4 content in the total mixed polyol esters.

In a further determination of the kinetic effects of esterification, a comparison of the process according to the invention with i-C4 acid in the form of the anhydride and subsequent i-C9 acid-esterification step was again carried out. The reaction time in the first step was kept at 1 h in the case of the anhydride. In the process not according to the invention using an acid in the first step, the reaction time was doubled to 2 h. The reaction times in the second step were varied (2-8 h). The percentages of the mixed PE esters (see reaction equation 1) and the percentages of i-C4 in the total mixture of polyol esters are given.

According to the invention:

| Ester composition | | Reaction time i-C9 [h] | | | |
|---|---|---|---|---|---|
| | | 2 | 3 | 5 | 8 |
| Proportion [mol %] | PE444-OH | 1.50 | 0.96 | 0.34 | 0.19 |
| | PE4444 | 2.57 | 2.20 | 2.36 | 1.33 |
| | PE449OH | 4.89 | 4.71 | 1.64 | 1.03 |
| | PE4449 | 6.44 | 8.74 | 10.35 | 9.01 |
| | PE499OH | 8.99 | 9.04 | 2.99 | 2.17 |
| | PE4499 | 11.73 | 17.73 | 23.14 | 22.63 |
| | PE999OH | 7.48 | 6.78 | 2.29 | 1.85 |
| | PE4999 | 15.39 | 21.63 | 30.76 | 32.48 |
| | PE9999 | 9.36 | 11.92 | 18.77 | 21.02 |
| | i-C4 content in ester components [mol %] | 44 | 42 | 40 | 36 |

Not according to the invention:

| Ester composition | | Reaction time i-C9 [h] | | | |
|---|---|---|---|---|---|
| | | 2 | 3 | 5 | 8 |
| Proportion [%] | PE444-OH | 0.76 | 0.52 | 0.21 | 0.14 |
| | PE4444 | 0.79 | 1.03 | 0.45 | 0.60 |
| | PE449OH | 5.12 | 3.56 | 1.83 | 1.24 |
| | PE4449 | 6.40 | 7.14 | 4.57 | 6.21 |
| | PE499OH | 11.06 | 8.06 | 5.27 | 3.00 |
| | PE4499 | 18.47 | 20.21 | 17.13 | 22.19 |
| | PE999OH | 8.07 | 6.12 | 5.30 | 2.50 |
| | PE4999 | 24.97 | 27.93 | 31.68 | 35.25 |
| | PE9999 | 13.09 | 15.62 | 23.76 | 21.06 |
| | i-C4- in ester component [mol %] | 37 | 37 | 30 | 33 |

It can be seen that by using the anhydride of the less reactive acid with a significantly shorter process time in the first process step (1 h i-C4 anhydride vs. 2 h i-C4 acid), mixed polyol esters with a comparably higher proportion of the less reactive acid are obtained. This is unusual in view of the long reaction times and high temperatures in the second process step with the more reactive acid.

The invention claimed is:

1. Process for the preparation of mixed polyol-carboxylic acid esters having a molecular weight greater than or equal to 200 g/mol and less than or equal to 1000 g/mol, characterized in that a polyol is reacted in an at least two-step reaction with different monocarboxylic acids in the form of monocarboxylic acids or of monocarboxylic acid anhydrides, wherein the different monocarboxylic acids being reacted with the polyol in the order of their reactivity in the esterification reaction, starting with the lowest reactivity, wherein the monocarboxylic acids with lower reactivities being reacted with the polyol as monocarboxylic acid anhydrides and the monocarboxylic acid with the highest reactivity being reacted thereafter as monocarboxylic acid.

2. The process according to claim 1, wherein two different monocarboxylic acids are reacted with the polyol, wherein in the first step the less reactive monocarboxylic acid is reacted with the polyol to greater than or equal to 70 mol % as a monocarboxylic acid anhydride.

3. The process according to claim 1, wherein the polyol has greater than or equal to 2 and less than or equal to 8 OH groups.

4. The process according to claim 1, wherein the polyol is an aliphatic polyol having a molecular weight of greater than or equal to 50 g/mol and less than or equal to 400 g/mol.

5. The process according to claim 1, wherein the different reaction steps are carried out without work-up in only one reaction solution.

6. The process according to claim 1, wherein the esterification is carried out without addition of an esterification catalyst.

7. The process according to claim 1, wherein the less reactive monocarboxylic acid is presented in the form of an anhydride and is first reacted with only a portion of the polyol, the remaining portion of the polyol being subsequently added together with the monocarboxylic acid or acids having the higher reactivity.

8. The process according to claim 2, wherein the less reactive monocarboxylic acid is a branched monocarboxylic acid with an alkyl group in the alpha position to the carboxylic acid group and the more reactive monocarboxylic acid is a branched or unbranched C4-C18 monocarboxylic acid without an alkyl group in the alpha position to the carboxylic acid group.

9. The process according to claim 1, wherein the less reactive monocarboxylic acid is iso-butyric acid and the more reactive monocarboxylic acid is iso-nonanoic acid.

10. The process according to claim 1, wherein the molar ratios of less reactive monocarboxylic acids or monocarboxylic acid of the most reactive monocarboxylic acid, each expressed as moles/mole of polyol, are greater than or equal to 1 and less than or equal to 3.5.

11. The process according to claim 1, wherein the temperatures in the different reaction steps are different, wherein the temperature in the first esterification step of the monocarboxylic acids with the lower reactivity 50° C. to 100° C. and is below the temperature in the last esterification step of the monocarboxylic acids.

12. The process according to claim 1, wherein the mixed polyol esters prepared comprise at least two different ester groups and a hydroxyl number greater than or equal to 0 and less than or equal to 10.

13. The process according to claim 12, wherein the mixed polyol ester prepared is an iso-butyric acid/iso-nonanoic acid ester of pentaerythritol.

14. The process according to claim 13, wherein the polyol ester has greater than or equal to 20 mol % and less than or equal to 50 mol % iso-butyric acid groups and greater than or equal to 50 mol % and less than or equal to 80 mol % iso-nonanoic acid ester groups.

* * * * *